United States Patent
McLaughlin et al.

(10) Patent No.: US 8,244,393 B2
(45) Date of Patent: Aug. 14, 2012

(54) SYSTEM AND METHODS FOR REGISTERING A CONTROLLED WEB TO A PITCHED UNIT OPERATION

(75) Inventors: Jon Kevin McLaughlin, West Chester, OH (US); Daniel Jon Amundson, Cincinnati, OH (US); Charles Phillip Miller, Cincinnati, OH (US); Jason Lee Debruler, West Chester, OH (US); Paul Anthony Kawka, Guilford, IN (US); Andrew Price Palmer, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 204 days.

(21) Appl. No.: 12/556,922

(22) Filed: Sep. 10, 2009

(65) Prior Publication Data

US 2011/0060447 A1    Mar. 10, 2011

(51) Int. Cl.
*G06F 19/00* (2011.01)

(52) U.S. Cl. .......................... 700/122; 702/94
(58) Field of Classification Search .................. 700/122; 702/94
See application file for complete search history.

(56) References Cited

U.S. PATENT DOCUMENTS

| | | |
|---|---|---|
| 3,165,056 A | 1/1965 | Heatley |
| 3,407,690 A | 10/1968 | Stanley |
| 3,739,968 A | 6/1973 | Bodendoerfer |
| 3,774,016 A | 11/1973 | Sterns et al. |
| 3,783,783 A | 1/1974 | Hamisch, Sr. |
| 3,952,746 A | 4/1976 | Summers |
| 4,019,306 A | 4/1977 | Evans |
| 4,022,456 A | 5/1977 | Hooper et al. |
| 4,081,301 A | 3/1978 | Buell |
| 4,294,644 A | 10/1981 | Anderson |
| 4,381,211 A | 4/1983 | Nechay |
| 4,384,500 A | 5/1983 | Firberg |
| 4,452,140 A | 6/1984 | Isherwood et al. |
| 4,452,659 A | 6/1984 | Geurtsen et al. |
| 4,511,425 A | 4/1985 | Boyd |
| 4,549,917 A | 10/1985 | Jensen, Jr. |
| 4,662,875 A | 5/1987 | Hirotsu et al. |
| 4,695,278 A | 9/1987 | Lawson |
| 4,719,575 A | 1/1988 | Gnuechtel |
| 4,735,622 A | 4/1988 | Acuff et al. |
| 4,757,930 A | 7/1988 | Ditto |
| 4,795,265 A | 1/1989 | Dahlberg et al. |
| 4,795,454 A | 1/1989 | Dragoo |
| 4,795,513 A | 1/1989 | Jensen, Jr. |
| 4,808,177 A | 2/1989 | DesMarais et al. |

(Continued)

FOREIGN PATENT DOCUMENTS

EP    0 938 422 B1    1/2001

(Continued)

OTHER PUBLICATIONS

PCT International Search Report, PCT/US2010/048388 date of mailing Dec. 27, 2010.

*Primary Examiner* — Michael D Masinick
(74) *Attorney, Agent, or Firm* — Charles R. Ware; Charles R. Matson

(57) ABSTRACT

Systems and methods for registering a web to an on-line pitched unit operation.

10 Claims, 9 Drawing Sheets

U.S. PATENT DOCUMENTS

| | | |
|---|---|---|
| 4,837,715 A | 6/1989 | Ungpiyakul et al. |
| 4,864,631 A | 9/1989 | Jensen |
| 4,963,140 A | 10/1990 | Robertson et al. |
| 5,008,110 A | 4/1991 | Benecke et al. |
| 5,019,066 A | 5/1991 | Freeland et al. |
| 5,026,464 A | 6/1991 | Mizuno et al. |
| 5,087,253 A | 2/1992 | Cooper |
| 5,136,316 A | 8/1992 | Punater |
| 5,235,515 A | 8/1993 | Ungpiyakul et al. |
| 5,286,543 A | 2/1994 | Ungpiyakul |
| 5,359,525 A | 10/1994 | Weyenberg |
| 5,615,468 A | 4/1997 | Chubbuck |
| 5,659,538 A | 8/1997 | Stuebe et al. |
| 5,708,341 A | 1/1998 | Ishida |
| 5,980,087 A | 11/1999 | Brandon et al. |
| 6,277,230 B1 | 8/2001 | Milko |
| 6,444,064 B1 | 9/2002 | Henry et al. |
| 6,553,270 B1 | 4/2003 | Houle et al. |
| 6,558,499 B1 | 5/2003 | Pargass et al. |
| 6,574,520 B1 | 6/2003 | Liu |
| 6,743,314 B2 | 6/2004 | Henry et al. |
| 6,764,563 B2 | 7/2004 | Henry et al. |
| 6,909,106 B2 | 6/2005 | Ungpiyakul et al. |
| 6,955,733 B2 * | 10/2005 | Miller et al. .................. 156/64 |
| 6,957,160 B2 * | 10/2005 | Miller et al. .................. 702/94 |
| 6,990,715 B2 | 1/2006 | Liu |
| 7,005,028 B2 | 2/2006 | Middelstadt |
| 7,123,981 B2 | 10/2006 | Dollevoet et al. |
| 7,172,666 B2 | 2/2007 | Groves |
| 2003/0047273 A1 | 3/2003 | Kojo et al. |
| 2003/0075029 A1 | 4/2003 | Franklin et al. |
| 2003/0136495 A1 * | 7/2003 | Miller et al. .................. 156/64 |
| 2003/0229325 A1 | 12/2003 | Belau et al. |
| 2005/0125180 A1 * | 6/2005 | Miller et al. .................. 702/94 |
| 2011/0060447 A1 * | 3/2011 | McLaughlin et al. ........ 700/124 |
| 2011/0113560 A1 * | 5/2011 | Receveur ......................... 5/706 |

FOREIGN PATENT DOCUMENTS

| | | |
|---|---|---|
| WO | WO 96/33054 | 10/1996 |
| WO | WO 00/45767 | 8/2000 |
| WO | WO 03/030083 A1 | 4/2003 |
| WO | WO 2004/060784 A1 | 7/2004 |

* cited by examiner

SYSTEM AND METHODS FOR REGISTERING A CONTROLLED WEB TO A PITCHED UNIT OPERATION

FIELD OF THE INVENTION

Various embodiments are directed to systems and methods for registering a controlled web to a pitched unit operation.

BACKGROUND OF THE INVENTION

Some machines align a moving web with another web or with a machine operation. This alignment process is called registration. Many of these machines perform registration with a control system.

The control system controls the machine. During registration, the control system sends a registration signal to the machine's moving parts. The machine responds to the registration signal by adjusting the moving parts. The adjustment aligns the moving web.

It is often desirable for a machine to respond to a registration signal in a consistent way. Unfortunately, some machines may respond to a registration signal in different ways at different operation speeds.

Many manufacturing operations include a number of manufacturing machines. These machines may be basically the same, except for some differences in mechanical configuration. For example, a manufacturing operation may have a first machine configured to run a smaller sized product and a second machine configured to run a larger size of the same product. It is often desirable for these machines to respond to registration signals in a consistent way. Unfortunately, such machines may respond to a registration signal in different ways.

BRIEF DESCRIPTION OF THE DRAWINGS

The above-mentioned and other features and advantages of the present disclosure, and the manner of attaining them, will become more apparent and the present disclosure itself will be better understood by reference to the following description of various non-limiting embodiments of the present disclosure taken in conjunction with the accompanying drawings, wherein.

DETAILED DESCRIPTION OF THE INVENTION

All references cited herein are incorporated herein by reference in their entireties. Citation of any reference is not an admission regarding any determination as to its availability as prior art to the claimed invention.

The present disclosure includes systems and methods for a machine to register a moving web with another web or with a machine operation. By using these systems and methods in a machine, the machine can respond to a registration signal in the same way at different operation speeds. By using these systems and methods in machines that are basically the same, except for some differences in mechanical configuration, the machines can respond to a registration signal in the same way.

As used herein, the following terms are defined as follows.

"Disposable absorbent article" means herein the following articles: a) baby articles including incontinence articles (such as disposable diapers, pull-ons, training pants), and other absorbent articles such as baby bibs; b) adult incontinence articles; and c) feminine hygiene articles.

Figure 1:
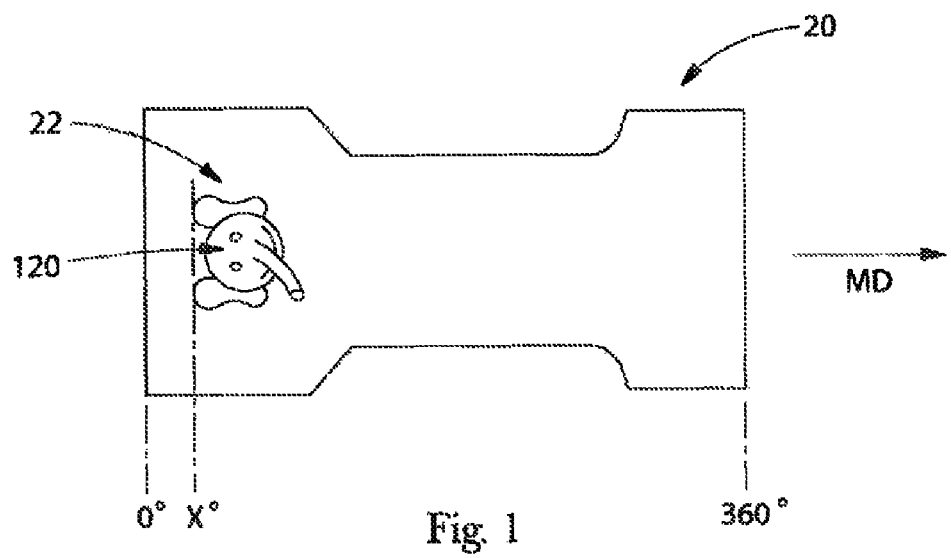
FIG. 1 is a plan view of one embodiment of a disposable diaper in a flat, uncontracted position showing a desired location for a pre-produced object (e.g., graphic).
Figure 4A:
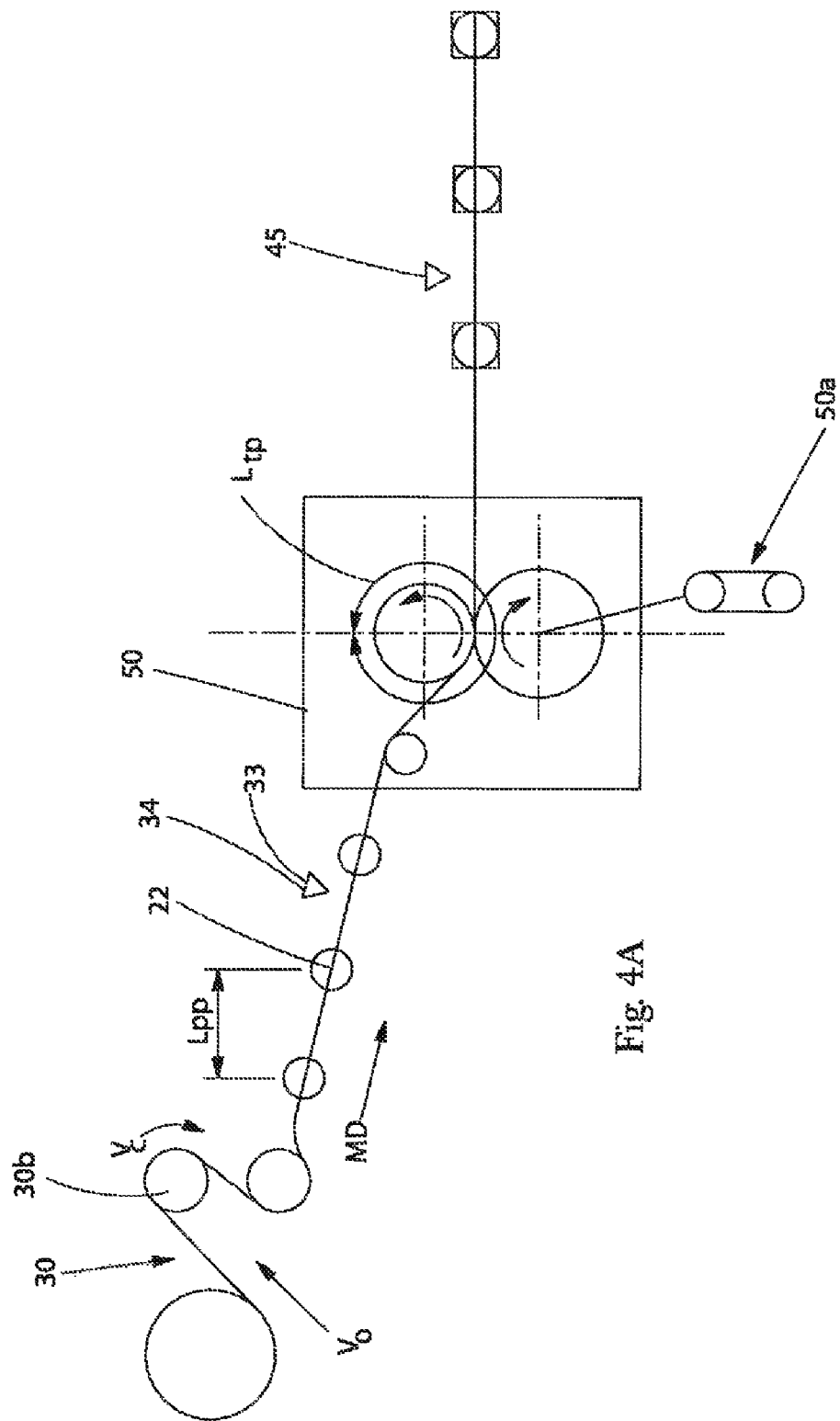
FIG. 4A is a schematic diagram of one embodiment showing the process of registering one controlled web to a pitched unit operation.
Figure 4B:
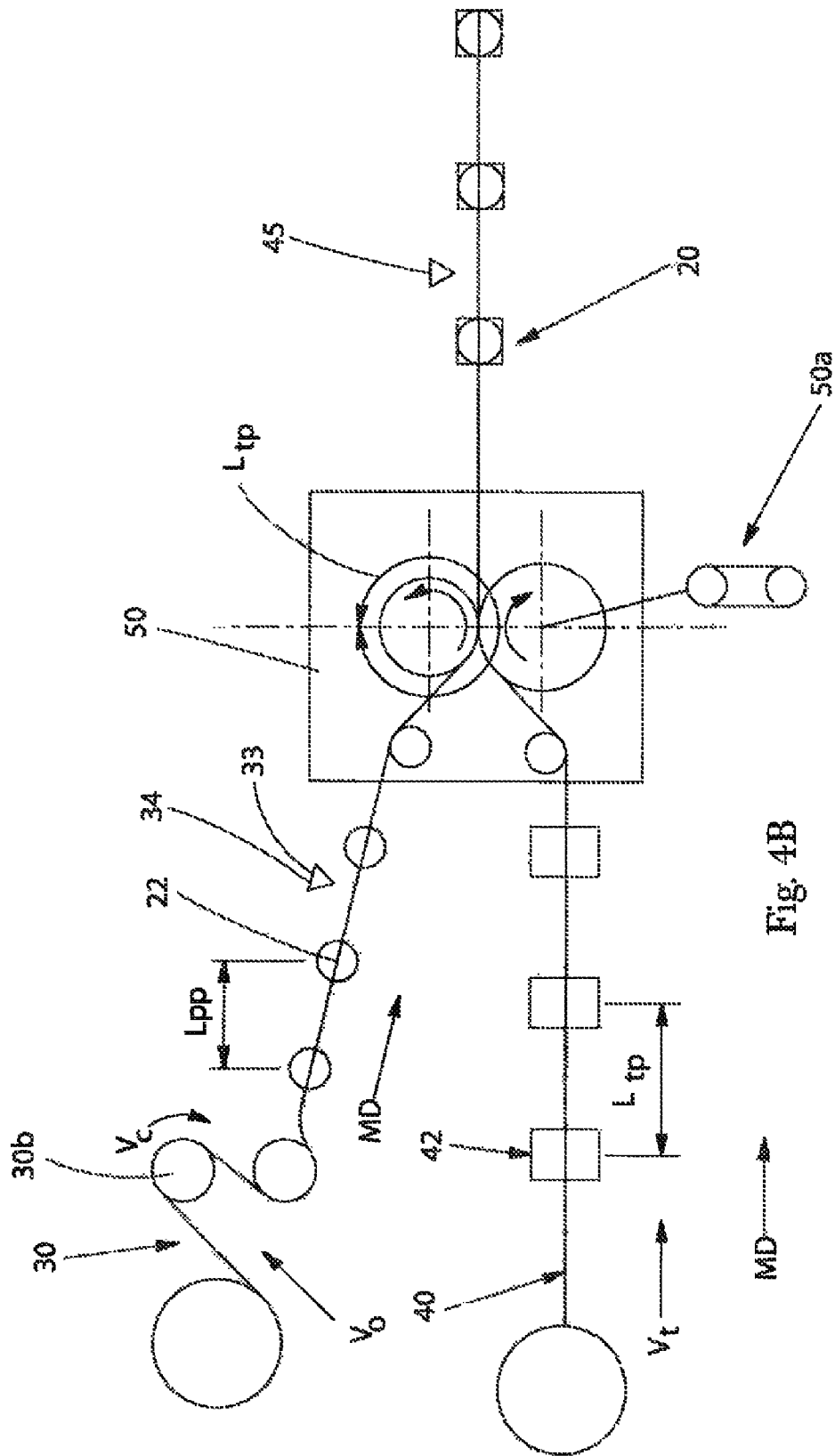
FIG. 4B is a schematic diagram of another embodiment showing the process of combining two simultaneously advancing webs.

"Machine direction" ("MD"), "web direction" or "web path" means the direction of movement of the product along a manufacturing line. The machine direction is shown in FIGS. 1, 4A and 4B.

"Product pitch length" means the length of material, on a relaxed basis, that runs the full length of the product under production. A product pitch for typical diaper products is illustrated as "PP" in FIG. 2B.

"Manufacturing cycle," "machine cycle," or "production cycle" means herein a cycle of a pitched unit operation to make a single product or other unit. Manufacturing cycle can be expressed in various ways including degrees of a full circle represented from 0° to 360°.

"Registration process," "registration system," "registration," or "registering" means herein an automatic machine control process or system for introducing a pre-produced web, (which can have multiplicity of pre-produced objects spaced on the web at a pitch interval varying in the web direction) to a pitched unit operation by providing an automatic positional adjustment of the pre-produced object on the web, functioning as a controlled web metered by a dependent axis (e.g., a web metering point), to a target position constant associated with the pitched unit operation.

"Phase", "phase relationship", or "in phase" refers herein to a positional relationship between two or more axes of repetitive motion. The above terms can be expressed in a degree of rotation or in linear terms in the machine direction. For example, the phase representation from 0° to 360° for a flat, uncontracted diaper 20 is shown in FIG. 1. The phase position of an object can be described in terms of any identifiable feature of the object. In FIG. 1, X° is representative of an exemplary desired phase position of the pre-produced object 22. "Phase" also refers to a change of a target position data or a setpoint variable of a controller.

"Registered graphics" refers to single or multiple colored graphic objects that can be printed on a web (an "off-line-made", "pre-produced" web) close to a specified pitch length on a relaxed web basis.

"Independent axis" can be a unit operation that can control one or more other unit operations, functioning as a master axis. An independent axis can be a pitched or a non-pitched unit operation. However, it should be understood that the independent axis can be also controlled by another independent axis. For example, in production of disposable absorbent articles, a combining unit can be controlled by an initial knife unit (for cutting a continuous material into discrete absorbent cores) and can at the same time function as an independent unit for controlling a web metering point unit (metering a controlled web).

"Dependent axis" can be a unit operation functioning as a slave axis controlled by an independent axis. Dependent axis can be a pitched or non-pitched unit operation.

"Target web" or "independent web" is an on-line or off-line made web, which includes a multiplicity of targets objects spaced in the machine direction. An example of a target web can include a web containing absorbent cores spaced longitudinally along the web.

"Target object" means any object on the target web or a target position of the pitched unit operation, related to the manufacturing of the product, made on-line on the converting line, being spaced longitudinally at a pitch interval.

"Target web pitch length" (Ltp) means the nominal repeat length longitudinally, in the machine direction between consecutively spaced target objects on the target web.

"Pitched unit operation" refers herein to a MD fabrication apparatus having a pitch related function for working one or more webs in the manufacture of disposable absorbent articles, a portion, or a component of a disposable absorbent article. For example, the unit operation can include, but is not limited to such pitched web working apparatuses as a severing or cutting device, an embossing device, a printing device, a web activator, a discrete patch placing device (e.g., a cut-and-slip unit), a web combining device, and the like, all of which have in common that they include a machine cycle corresponding to a product pitch length (e.g., a circumference or a trajectory movement of a rotary cutting device, a combining device and the like).

"Actual position data" means an actual position of a pre-produced object on a moving web.

"Actual bias position data" means an actual bias position of a pre-produced object on a moving web relative to the machine cycle of the pitched unit operation.

"Target position constant" means a constant position value provided to the registration control system associated with the machine cycle. The target position constant can be any desired or selected position within the manufacturing cycle.

"Target bias position constant" means a constant position reference value provided to the registration control. The target bias position constant can be any desired or selected position within the manufacturing cycle.

"Controlled web", "off-line-made", or "pre-produced web" means a web to be introduced into a converting line producing disposable absorbent articles, the web containing a multiplicity of pre-produced objects which are spaced at a pitched interval in the web direction; the controlled web can be manipulated (e.g., by changing strain or flow rate) by the control method of the present invention as needed to register the pre-produced object on the web in relation to a desired target position constant.

Figure 7:
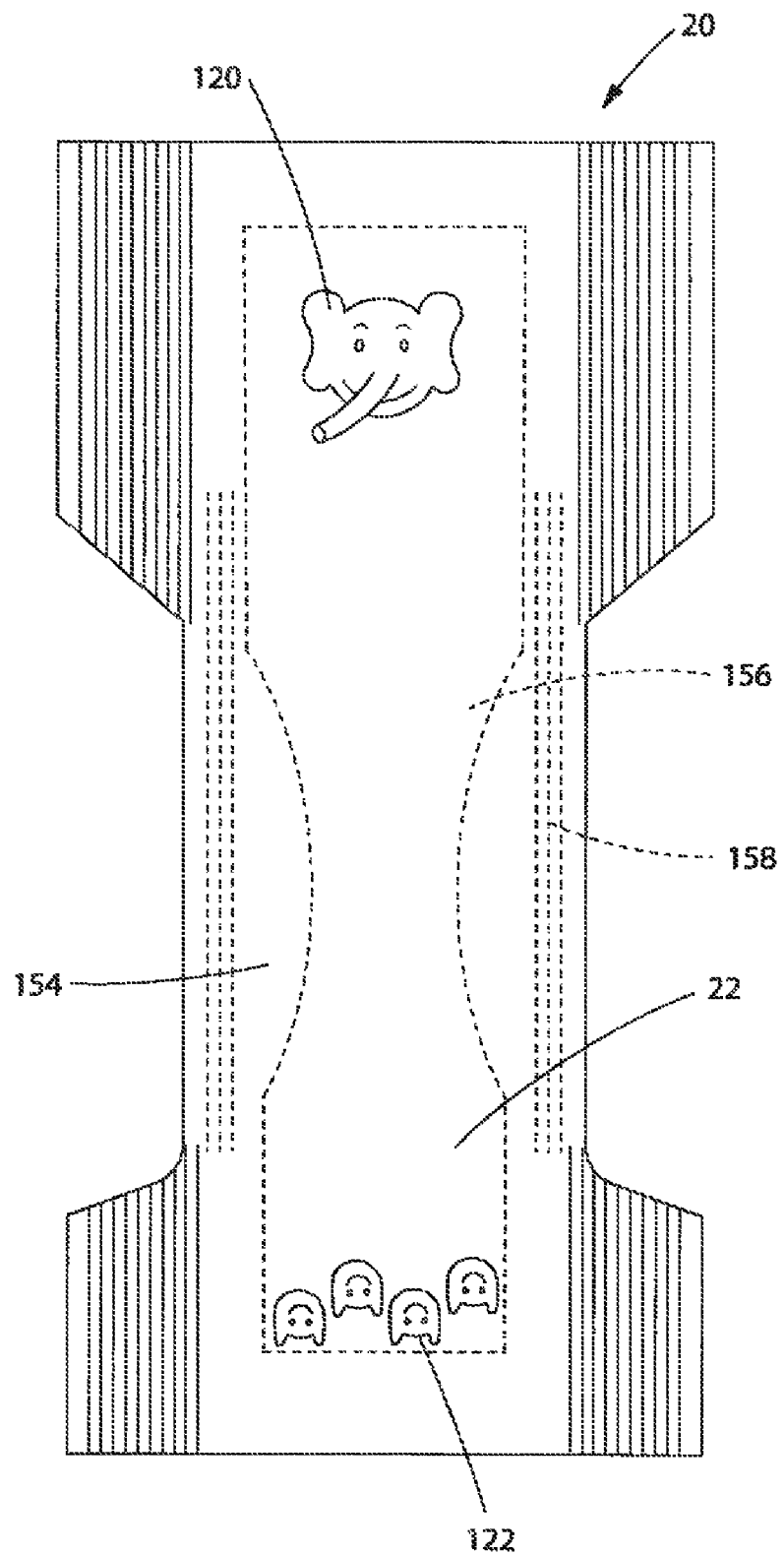
FIG. 7 is a simplified plan view of another embodiment of a disposable absorbent article having registered graphics.

"Pre-produced object" herein means the pre-produced object on a web produced off the converting line on a separate independent process not control-linked to the process of the converting line, and spaced at pitch intervals in the web direction. The term "pre-produced object" as used herein refers to any object or physical property, visible or normally invisible to the human eye, pre-bonded, pre-applied, pre-cut, pre-glued, pre-activated, pre-embossed, or any combination thereof within a single product pitch Lpp. For example, a pre-produced object 22 comprising of graphics 120 and 122 of a disposal article, (as shown in FIG. 7) of disposable absorbent articles. Furthermore, the term "pre-produced object" also can refer to a registration mark specifically provided for the purpose of registration. The registration mark may be both visible and normally invisible to the human eye.

"Controlled web pitch length" means the repeat length in a machine direction (MD) between consecutively spaced pre-produced objects on the controlled web.

In the manufacture of disposable absorbent articles such as diapers and feminine hygiene products, it is a common manufacturing practice to combine continuously moving webs and/or to perform a regular repeating operation, such as cutting, printing, etc., to a single web. The webs are typically represented by plastic films, non-wovens, elastics, etc., supplied to a converting line in their original production form and do not require special positioning before combining with other materials on the converting line. However, the manufacture of disposable absorbent articles may benefit if the above materials are supplied to the converting line as pre-produced materials or objects (e.g., objects produced off the converting line and carrying various elements of disposable absorbent articles consecutively spaced along the web length at a nominal pitch length). The pre-produced objects may be provided to the regulator repeating operation either as a continuous web, or as discrete non-continuous objects (e.g., after the application of a cutting operation). Because the pitch length between the consecutively spaced elements of the pre-produced materials can vary at small but significant variations, there is a demand for a method to register the consecutively spaced pre-produced elements in relation to desired positions, combining the pre-produced materials into a final article or product, in order to ensure consistent positioning of the product elements in every absorbent article.

For example, pre-produced breathable polymer films made off the converting lines that are particularly useful as backsheet materials for disposable absorbent articles typically have good surface characteristics that make them suitable for the application of multi-colored, high resolution graphics. Such films, however, tend to be mechanically unstable with a particular tendency toward thermal shrinkage in the machine direction, commonly understood as a steady state disturbance. These instabilities contribute to the difficulty in correctly positioning the pre-produced objects (e.g., graphics) on the polymer web in relation with a desired, target position on a disposal absorbent article.

Control systems are used to register continuous and non-continuous pre-produced objects to combinatory and non-combinatory operations. Existing control systems, however, require controller gains to be set specifically for each unique system setup based on empirical data gathered from field measurements. This requires considerable effort and expense for each individual operation.

Various embodiments of the present invention are directed to systems and processes for registering off-line made pre-produced webs in relation to a target position on a disposable absorbent article. The pre-produced objects on a web spaced at pitched intervals which include variations or disturbances may result, for example, because it is virtually impossible to maintain a constant web tension during pre-producing (due to machine variations) and then in a roll form (due to inherent tension differential among web layers of the roll), as well as climatic conditions affecting, for example, mechanically unstable microporous polymer films during storage.

In various embodiments, the continuous registration system disclosed herein performs two functions simultaneously in order to correctly register pre-produced webs to a target position. First, it continuously corrects the pre-produced pitch length, or spacing of the pre-produced objects on the controlled web, to match the pitch length of the target object. Second, it continuously synchronizes the phase positions of the two such that they are combined in the proper position, e.g., such that the graphic 22 is correctly located as desired on the diaper 20, for example, in substantially the positions shown in FIG. 1, 7 or 8.

According to various embodiments of the registration control system, a PI controller may be used to modify the feed velocity of the controlled web to allow for variations in controlled web pitch and phase differences between the controlled web and a pitched unit operation or operations. For each pre-produced object, the PI controller may receive as input an error signal representing a difference between an actual position bias and a target position bias for a pre-produced object. The integral term of the PI controller may be found by integrating previous error signals, not over time, but over pre-produced objects. For example, the integral term may be proportional to the sum of all or a portion of error signals generated based on previously processed pre-produced objects. The output of the PI controller may be generated and/or sampled once per pre-produced object. In this way, the closed-loop dynamic performance of the registration system may be such that the controller may provide consistent performance in terms of the product independent of line speed, specific equipment setups and many other application details. This may allow registration problems to be handled from the same framework instead of requiring unique tailoring for each setup. In this way, controller attributes such as the proportional and integral terms may be found according to classical control theory based on the closed-loop performance. Accordingly, the registration system may provide simpler and more robust performance than existing systems that may require controller attributes to be set in the field with limited knowledge of the specific closed-loop dynamic performance.

In addition, according to various embodiments, the output of the PI controller may be multiplied by a nominal gear ratio of the controlled web. The nominal gear ratio of the controlled web may represent a ratio of a position of the controlled web over a position of the pitched unit operation. The gain of the registration process is proportional to the inverse of the nominal gear ratio. Accordingly, scaling the output of the PI controller by the nominal gear ratio may cancel the process gain, leading to more precise control.

It is noted that any other polymer films, non-woven or woven webs, etc., capable of stretching under a tension force applied along the web path, can be useful as controlled webs herein. It is also noted that although the description of embodiments contained herein is primarily given in the context of a diaper converting line, e.g., registration of pre-produced objects phased to diaper cores or a pitched unit operation (target objects) on a diaper converting line, it will be understood by those of skill in the art that the registration process herein may be used to register webs in any application.

Where webs each carrying phased objects must be combined in a predetermined relationship, information pertaining to the phase position of the target web, usually the product under production, e.g., the diaper chassis assembly, must be fed to the registration process. In addition, the position of the pre-produced objects (such as a pre-produced graphics or registration marks on a polymer backsheet web or a non-woven topsheet) on each incoming, controlled web which is to be combined with the target web must also be known and fed. As previously noted, the target web pitch length and the controlled web pitch length are rarely identical. It will be understood by those of skill in the art that any incoming fed web may be designated as a target web or a controlled web, and processed accordingly. Likewise, in embodiments where the pitched unit operation does not include the combination of multiple webs, the registration process may be implemented by modifying the feed characteristics of the controlled web, or by modifying a speed of the pitched unit operation.

Figure 2A:
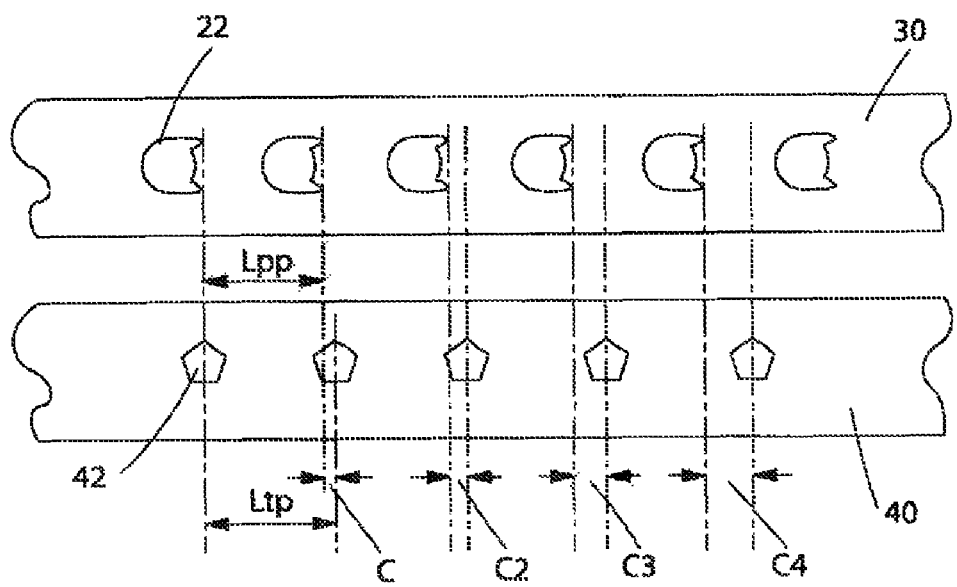
FIG. 2A is a schematic diagram showing simplified representations of a portion of a continuous diaper backsheet web having consecutively spaced pre-produced objects (e.g., preprinted graphics) thereon and a portion of a diaper product web.
Figure 2B:
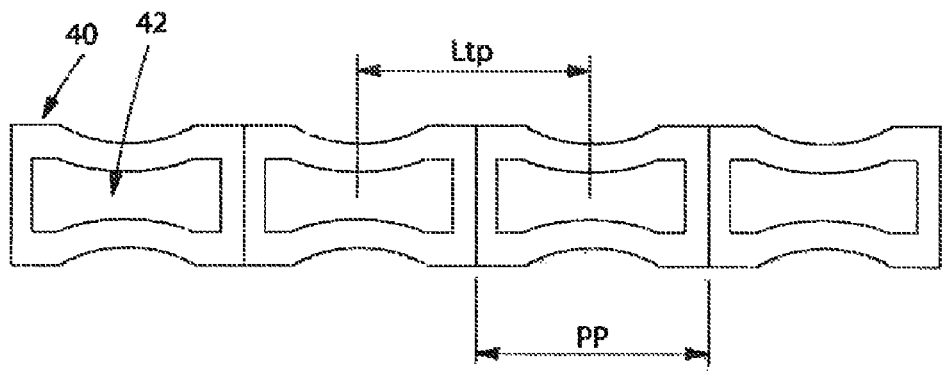
FIG. 2B is a top view of a diaper product web including a representation of the diaper core area.

The target object may comprise that part of the diaper chassis itself that is generally continuously comprised of the core and topsheet assembly, prior to the attachment of the backsheet web. FIGS. 2A and 2B show a target web 40 including target objects 42 consecutively but not necessarily equidistantly spaced thereupon at a target web pitch length, "Ltp". FIGS. 2A, 2B show the Ltp in two representations; the first one, as a pitch between target objects on the target web 40. One example of Ltp as a pitch between target objects 42 may be the pitch between the absorbent cores on the target web 40, and another example may be a circumference of a rotating element working the web of the pitched unit operation 50.

It is noted that the target object position may be directly sensed or inferred from the use of an electronic strobe. When the system is first started up, the operator may input an offset value using an "advance/retard" button while examining the position of the controlled web graphic using an actual strobe light, reading the finished product, or using a vision system that is strobed once per product. Once the offset value or target position bias is set, the registration system will target the controlled web pre-produced object to the same point in the machine cycle.

Again referring to FIG. 2A, the controlled web 30 may comprise a continuous film material, for example, a breathable microporous polymer film, that is used as part of the diaper backsheet. The controlled web 30 has pre-produced objects 22, consecutively but not equidistantly printed thereupon at a particular controlled web pitch length, "Lpp". Lpp is invariably something other (either longer or shorter) than both the product pitch length PP and the pitch length of the target web Ltp due to climatic conditions, thermally induced creep, and the like. An exemplary Lpp is shown in FIG. 2A. Pre-produced objects 22 may be registered graphics that are colorful, high resolution designs that are appealing to the consumer, who is typically a care-giver to the wearer of the diaper, or who in other cases may actually be the wearer.

As noted above, in most cases, Ltp is not equal to Lpp; in fact, exact matches are highly improbable. This difference is a major source of the difficulties associated with proper phasing of the controlled web 30 and the target web 40. As can be most clearly seen in FIG. 2A, a pitch delta C (e.g., Ltp minus Lpp) usually exists and must be corrected in order to insure proper product phasing. It is additionally noted that the pitch delta C associated with Ltp and Lpp typically accumulates for each subsequent target object 42, and thus a greater amount of correction is generally needed. This error accumulation of pitch delta is represented in FIG. 2A as C, C2, C3, C4. The corrections of pitch delta C, C2, etc. associated with the registration systems disclosed herein may not actually be necessary for product functionality; however, they may be important for consumer acceptance of the diaper products produced.

Figure 2C:
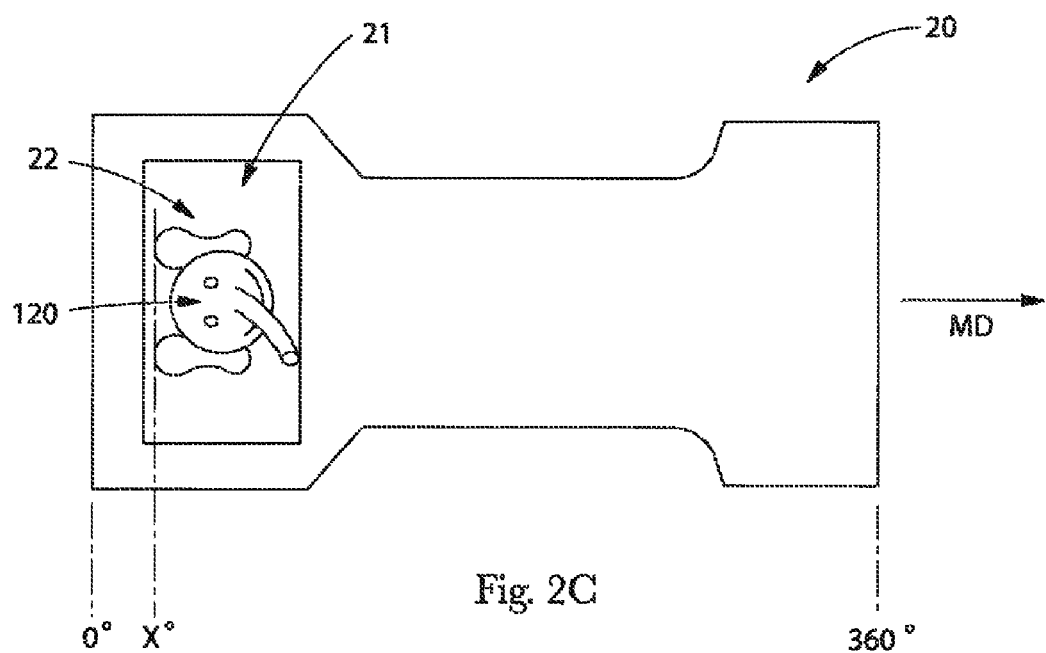
FIG. 2C illustrates one embodiment of the diaper of FIG. 1 after the application of an example landing zone.

According to various embodiments, the controlled web, instead of being maintained as a continuous material stream prior to being combined with the target web, may be discretized or turned into discrete elements. This may occur either before or after the pitched unit operation. Such a discretized portion of the controlled web may be referred to as a landing zone. FIG. 2C illustrates one embodiment of the diaper 20 after the application of an example landing zone 21. In the pictured embodiment, the landing zone 21 is a rectangular patch that may be applied to every product on the target web. The machine direction length of the landing zone may be considerably less than the total length of the product on the target web. Accordingly, the registration system may be configured to ensure that one full, discrete graphic is provided once per product and in the proper location.

Figure 3:
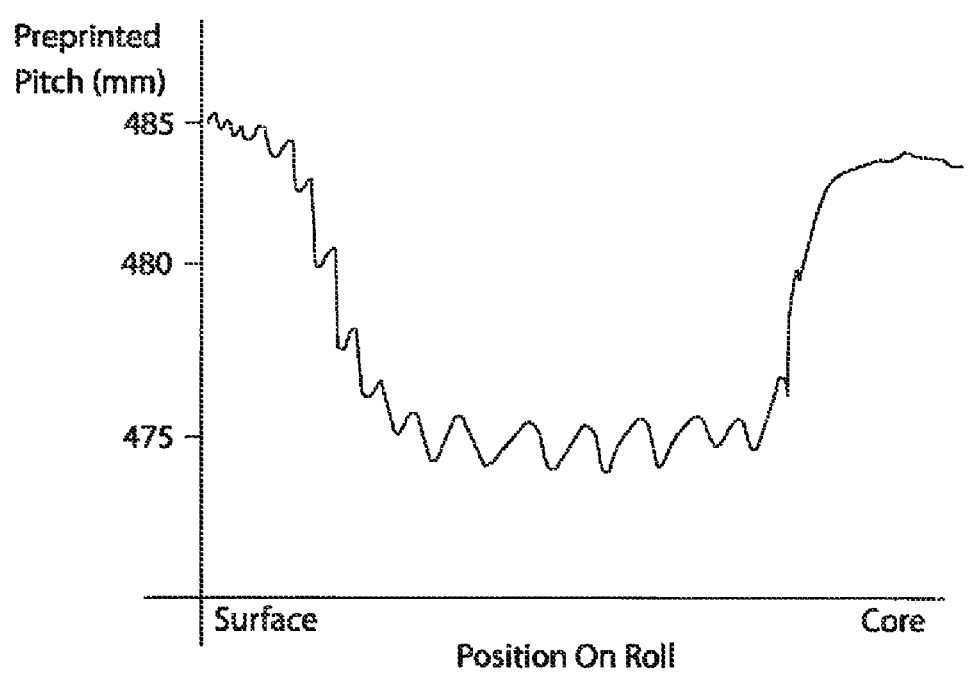
FIG. 3 is a graphical representation of the pitch length variation that may be experienced by pre-produced microporous materials that have been subjected to typical conditions of winding and warehouse storage.

FIG. 3 illustrates the instabilities in controlled web pitch length Lpp that may arise due to the inherent thermal instability of the microporous polymer films of the present invention. Such thermal instability leads to differential shrinkage of the microporous film, and significant variations in Lpp frequently result. Referring to FIG. 3, the position along a wound roll (e.g., a continuous, controlled web 30) of microporous polymer film that has been pre-produced with registered graphics is represented on the X axis. The start of the roll is indicated at the origin of the axes, while moving to the right along the X axis indicates moving toward the core of the roll, corresponding to unwinding the roll. On the Y axis, pre-produced pitch length Lpp is represented in millimeters. As can be seen, differences in pre-produced pitch lengths Lpp of up to about 10 mm may be seen between various locations on the same web of material.

The registration processes disclosed herein are thus designed to overcome the phasing problems associated with combining the target web 40 and the controlled web 30 where Ltp is not equal to Lpp, where Lpp is inherently variable, and where both webs are simultaneously and continuously fed to a combining operation. The processes may have the ability to on-goingly adjust the pitch length of the controlled web 30 as delivered to match or to more closely approximate that of the target web 40 or pitched unit operation. In addition, the system of the present invention may make such corrections in a gentle, non-abrupt and gradual fashion so as to account for the delicate nature of the web, which may be a microporous polymer film, without damaging it. Alternatively, if conventional higher strength webs are used, the system may be capable of making more rapid and abrupt adjustments that may not be acceptable with the microporous polymer films.

As described more fully below, this is accomplished by changing the velocity or flow rate of the controlled web 30 as well as by the use of web tension transients that may change the pre-produced pitch length Lpp of the pre-produced objects on the controlled web 30. The tension in the controlled web may be changed by differentially modifying the speed of the rollers and/or conveyor controlling the web (e.g., by changing the speed of one or two rollers close to the pitched unit operation). Changing the tension in a web causes a change in the pitch length of the web. Thus, more tension stretches the material of controlled web 30, causing the pitch length Lpp to increase, while less tension relaxes the controlled web 30, causing the pitch length Lpp to decrease. The absolute tension in the controlled web 30 should not approach zero tension, as control of the controlled web 30 would be lost. The velocity or flow rate of the controlled web 30 may be modified by cascading changes to the speed of rollers or conveyors throughout the system controlling the controlled web 30.

The system of the present invention thus introduces small tension transients, which provide on-going correction. This serves to maintain the integrity of the delicate, mechanically unstable polymer films that are useful for disposable absorbent articles herein. It also serves to correct the phase relationships of objects on the each incoming web in increments that are too small to be detected by the web handling process, which means that there is little possibility for the amount of error to become large enough to trigger the shut-down functions of the web handling process. In addition, it allows for manufacture of consecutive products that may have insignificant differences in the locations of the pre-produced objects on each product.

According to various embodiments, a PI control algorithm/controller is used to control the feed rate of the controlled web 30 only as necessary to minimize the actual position bias. The actual position bias may be found using any suitable sensor or method, for example, as described below. The system may sense a distance between a fixed position of converter machine time with user-set offset and the actual position of the pre-produced object (e.g., based on sensed marks indicating each pre-produced object). If the space between the sensed marks of the controlled web 30 (Lpp), is longer than the target pitch length Ltp, more web 30 is fed to the process, reducing the web tension and allowing the space between pre-produced objects to contract. Conversely, if the space between the sensed marks of the controlled web 30 is too short, less web is fed, causing an increase in web tension causing the space between marks to increase. In this way, not only is the pitch of the web brought close to the pitch of the product, but the position of the pre-produced object is brought close to the target position.

To determine the position of the pre-produced objects on controlled webs various detectors/scanners may be used, such as detectors/scanners capable of detecting changes in electromagnetic or acoustic fields. For example, to determine the position of the pre-produced object (e.g., color graphic) on the incoming controlled web 30, a sensor 34 is selected which detects differences between light passing through the web via different printed colors. The color of the target web object, the position of the target web object relative to other objects of the same color, and the size of the target object combine to create the means for generating a clean signal whose position is strobed once per machine cycle. Alternative means of establishing position of pre-produced objects include: 1) sensing a visible timing mark on a part of the web that can be later removed by the process; 2) sensing a normally invisible to the human eye registration mark which may or may not remain a part of a final article or product; 3) using a grid of sensors to look for a recognized pattern of light diffusion or 4) using an array of sensors, as in a machine vision system to look for a recognized pattern contained in an electro-magnetically or acoustically generated image.

The registration system disclosed herein may adjust the pitch Lpp of the controlled web 30 by on-goingly adjusting the tension in the controlled web 30. The Lpp is adjusted to "Lc", which is used herein to mean, length at combining, or length at the pitched unit operation. Lc is equal or approximately equal to Ltp, (e.g., the pitch length of the controlled web 30 is made approximately equal to that of the target web 40 so that the pre-produced object 22, can be positioned in the correct phase relationship to the product). This tension acts through the web modulus, Ew, of the controlled web 30, according to the following equation:

$$Lc = (1+\epsilon) \times Lpp = (1+T/Ew) \times Lpp, \qquad (1)$$

where:
$\epsilon$ = strain;
T = controlled web tension; and
Ew = web modulus of controlled web.

Equation 1 acts for all webs being combined together. Thus in the case of two webs:

$$Lc1=(1+T1/Ew1)\times Lpp1 \text{ and } Lc2=(1+T2/Ew2)\times Lpp2. \quad (2)$$

As noted above, at the point of registered combining under steady state conditions, Ltp is equal to Lc. Thus, the ratio of the relaxed lengths combined at any time is given by equation 3 below:

$$Lpp1/Lpp2=(1+T2/Ew2)/(1+T1/Ew1). \quad (3)$$

The tension variables T as well as the modulus variables Ew each have a range of variation, so the ratio of the Lpp values will always vary somewhat from unity. The difference between the Lpp ratio and unity is referred to herein as "puckering":

$$\text{Puckering \%}=(Lpp1/Lpp2-1)\times 100. \quad (4)$$

The selection of the raw material to be used for the backsheet, e.g., the controlled web 30, may be constrained by both the product design and the registration system of the present invention. The key parameters that may be unique to pre-produced objects are impacted by the needs of product functionality. For diaper backsheet, the material may be a breathable microporous polymer film. The microporous polymer film may be formed from a mixture of polyethylene and calcium carbonate, and titanium dioxide if needed to increase the white appearance of the film, since whiteness is a film characteristic that is necessary for widespread consumer acceptance. More preferably, the microporous polymer film has high thermal stability characteristics in order to support the printing of high resolution color graphics thereon. Preferably the film meets a maximum of ±1% repeat pitch variation, i.e., mismatch, but more typically ±2% is likely to be seen.

FIG. 4A is a schematic diagram of one embodiment showing the process of registering one controlled web to a pitched unit operation. According to various embodiments, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b. The actual position data is provided by detection of the position of a pre-produced object 22 on the controlled web 30 moving in the machine direction MD. Capture of the actual position data may occur automatically at a pre-produced object detection stage 33 via a sensor 34, providing actual position data of the pre-produced object 22. The machine cycle position of the pitched unit operation 50 may be found by electronically strobing a resolver 50a or other position sensing device (e.g., an encoder). A target position bias constant of the pre-produced object 22 may be provided by an operator. The target position bias constant may be a desired position value within the manufacturing cycle of the pitched unit operation 50. Alternatively, the target position bias constant may be provided automatically via any suitable detection device capable of sensing the position of the pitched unit operation 50.

FIG. 4B shows a schematic diagram of the process of an additional embodiment of registering the pre-produced web of the present invention. In the second embodiment, the registration system is a feedback control system requiring a comparison of an actual position of the pre-produced object 22 on the controlled web 30 to a target object position in relation to the finished product or the pitched unit operation 50. The controlled web 30 is initially fed at a velocity Vo, by a metering point 30b, and the target web 40 is fed to the combining pitched unit operation 50 at a velocity Vt. The actual position data is provided by detection of the position of a pre-produced object 22 of the controlled web 30 moving in the machine direction MD, can occur automatically at a pre-produced object detection stage 33 via a sensor 34. A resolver 50a may also be strobed to provide a corresponding machine cycle position of the pitched unit operation that may, in turn, be used to find a target position bias (see FIG. 5A). Detection of a target object 42 (e.g., diaper core) on the target web 40 moving also in the machine direction MD, can occur at the product detection stage 45 by an operator manually setting the target position constant. According to various embodiments, the resolver 50a mounted on the pitched unit operation 50 serves as the master reference for the metering point 30b. This master/slaved relationship serves as a feedforward path for the registration system 600 shown in FIG. 5B.

Figure 5A:
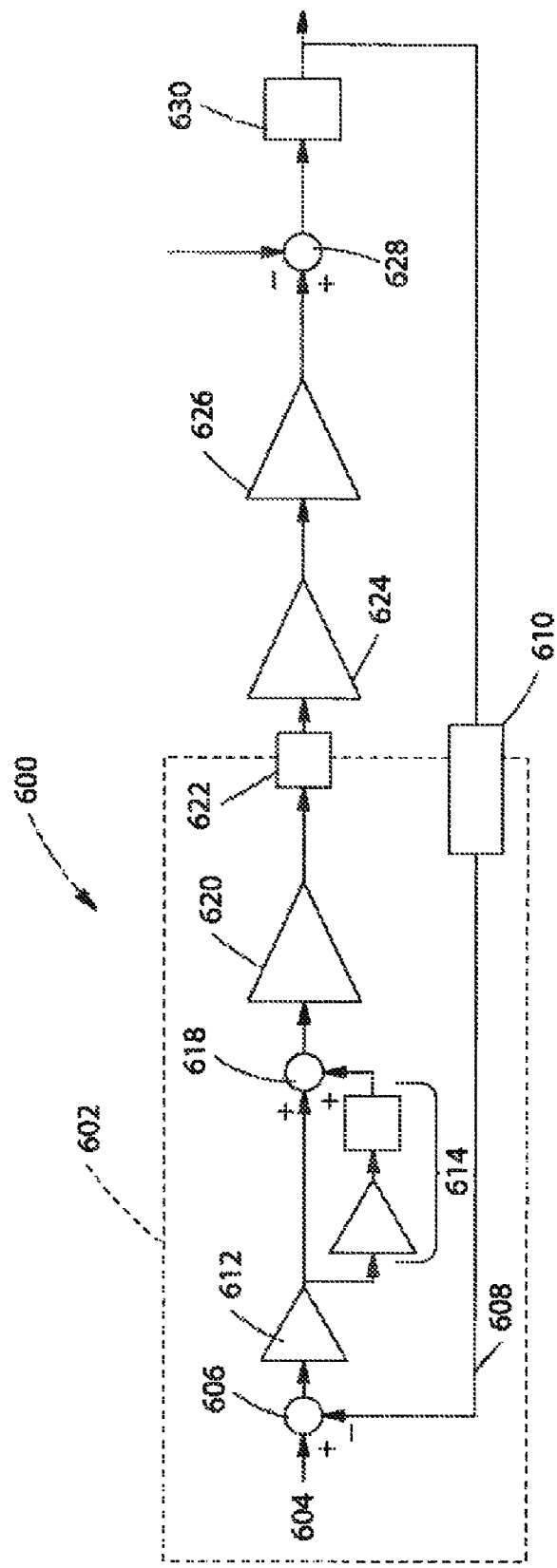
FIG. 5A is a schematic diagram of one embodiment of a registration control system.

FIG. 5A illustrates one embodiment of a registration control system 600. The control system 600 may take as input a target position bias constant 604, which may represent a desired position of the pre-produced objects 22 relative to the machine cycle of the pitched unit operation 50. For example, when the pitched unit operation 50 is a combination of a controlled web 30 and a target web 40, as shown in FIG. 4B, the target position bias constant 604 may represent a desired position of the pre-produced objects 22 relative to the position of target objects on the target web 40. When the pitched unit operation 50 operates on the controlled web 30 only, for example, as shown in FIG. 4A, the target position bias constant 604 may represent the desired position of the pre-produced objects 22 relative to the place on the controlled web 30 where the pitched unit operation 50 is to take place. The target position bias constant 604 may be pre-configured or set by an operator in the field, for example, as described above.

In addition to the target position bias constant 604, the control system 600 may receive as feedback input an actual position bias 608. The actual position bias 608 may represent an actual position of pre-produced objects 22 relative to the machine cycle of the pitched unit operation 50. The actual position of the pre-produced objects 22 may be found by the detection stage 33, as described above with respect to FIGS. 4A and 4B. The machine cycle position may be found by any suitable sensor including, for example, an encoder or resolver 50a. The actual position bias 608 may be found by taking a difference between the actual position and the machine cycle position.

The target position bias constant 604 and actual position bias 608 may be provided to a controller 602 of the control system 600, which may, according to various embodiments be and/or comprise a PI controller. Referring to FIG. 5A, the controller 602 may comprise a summing junction 606 where the actual position bias 608 is subtracted from the target position bias constant 604. The result may be an error signal. A proportional term 612 and an integral term 614 may applied to the error signal and the results may be summed at summing junction 618 to generate a correction signal u(k). The correction signal may be represented by Equation (5) below:

$$u(k) = \left[ K_{OP} + (K_{OP} * K_{OI}) * \frac{T_P * z}{z-1} \right] * e(k) \quad (5)$$

In practice, the correction signal u(k) may be represented as a discrete time/digital representation. In Equation (5), $T_P$ may represent a number of product or pitched unit operation periods. In embodiments where the correction signal is generated once per product, $T_P$ may be equal to one. The proportional 612 and integral 614 terms ($K_{OP}$ and $K_{OI}$) may be derived in any suitable manner including, for example, as described below. According to various embodiments, the integration variable of the integral term 614 may be pre-produced objects, or multiples thereof, instead of time. In discrete embodiments, the integral term 614 may be proportional to a sum of error signals taken over previously measured pre-produced objects. According to various embodiments, the integral term 614 may include or exclude the error signal corresponding to the currently measured pre-produced object.

The correction signal may be scaled by a nominal gear ratio 620, resulting in a gear ratio trim. The nominal gear ratio 620 may be an indication of the translation of the controlled web over the translation of the pitched unit operation. The nominal gear ratio may be expressed in terms of (rotary units/master units) where rotary units represent a translation of the controlled web and master units represent a corresponding translation of the pitched unit operation. According to various embodiments, the nominal gear ratio may be expressed as shown in Equation (6) below:

$$NGR = \frac{K_{ru} * K_{tp}}{K_{mu}} \qquad (6)$$

$K_{ru}$ is a translation of rotary units of the controlled web to meters. $K_{tp}$ is the target product pitch of the controlled web expressed in (meters/product). $K_{mu}$ is an expression of master units of the pitched unit operation per product expressed in (master units/product). Scaling the error signal by the nominal gear ratio 620 may cancel gains inherent to the registration process.

The controller 602, according to various embodiments, may be configured to operate once per pre-produced object. For example, as described above, the integration variable of the integral term 614 of the controller 602 may be pre-produced object periods rather than time. Also, the controller 602 may update once per pre-produced object. For example, a zero order hold 622 may be positioned to hold the output of the controller 602 between updates.

Gain 624 represents an ideal process gain of the registration process, which is expressed as the inverse of the nominal gear ratio described above. The process gain 624 may be inherent to the registration process and may be applied to the gear ratio trim in whole or as various components at different stages of the registration process. The correction signal may be scaled by the nominal gear ratio 620, as described above, to cancel out the process gain 624. It will be appreciated that the nominal gear ratio gain 620 may be applied inside the controller 602, as shown, or outside of the controller 602.

At 626, a master product velocity gain, $K_{PPS}$, may be applied. The master product velocity gain $K_{PPS}$ may represent a velocity of the pitched unit operation in products per second. When one pre-produced object is applied to each product, or in embodiments where a pitched unit operation operates once per pre-produced object, $K_{PPS}$ may also be expressed in terms of pre-produced objects per second. The result of applying the $K_{PPS}$ may be a trim velocity. The trim velocity may be used to adjust the velocity of the metering point 30b controlling the velocity of the controlled web 30. A summing junction 628 may add values representing non-idealities in the registration system due to disturbances in the pitched unit op, the controlled web feed actuator, the controlled web itself, etc. These non-idealities may be effectively summed with trim velocity to generate the actual velocity of the pitched unit operation relative to the velocity of the controlled web. Effects of the registration process are modeled as shown in 630. The result is the machine cycle position of the pitched unit operation relative to the position of the pre-produced objects on the controlled web. This is then sampled by sampler 610 and received as feedback input 608 at the controller 602, as described above. In the model 630, $T_D$ may represent a dead-time of the process.

Figure 5B:
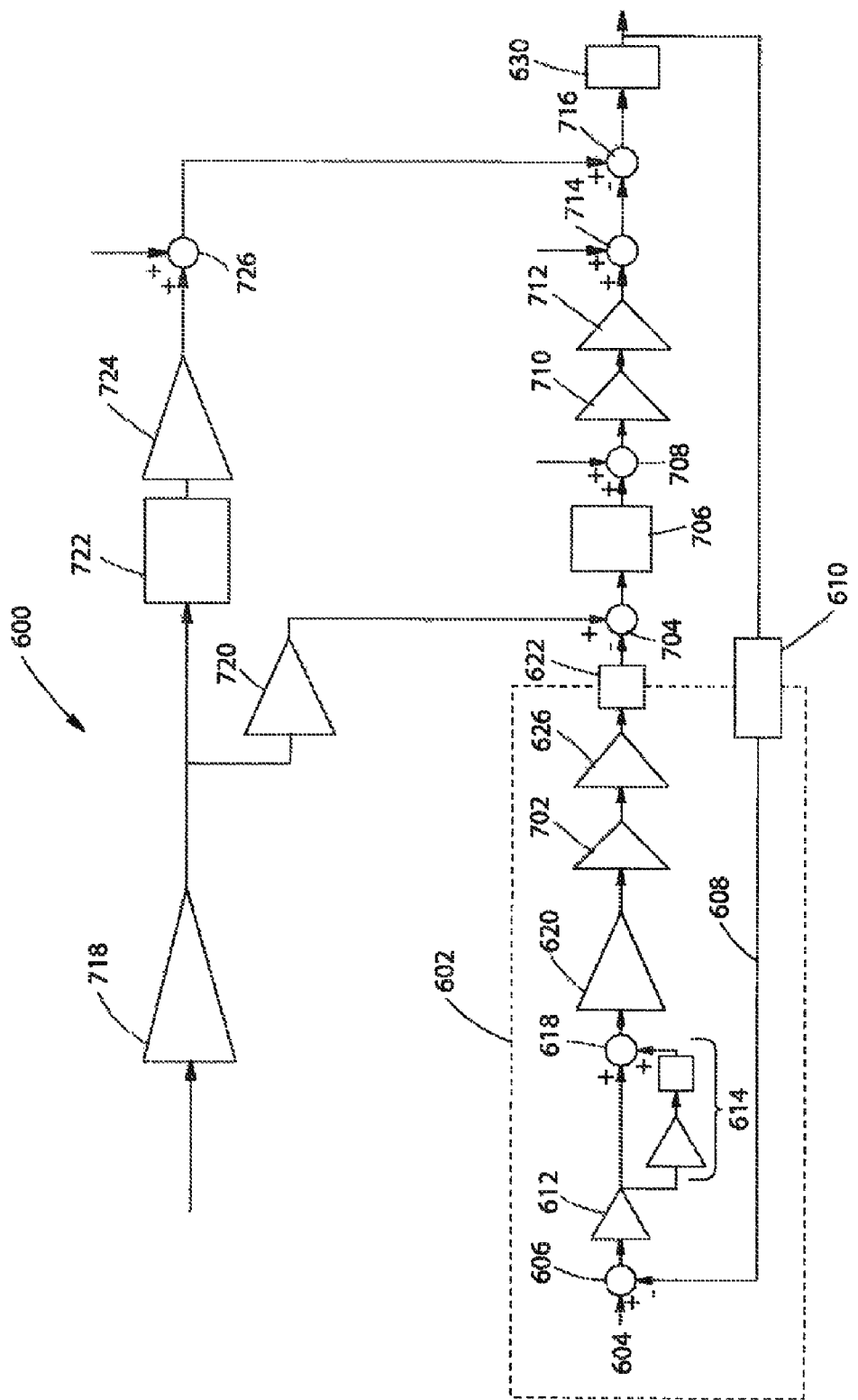
FIG. 5B is a schematic diagram of another embodiment of the registration control system of FIG. 5A.

FIG. 5B illustrates an additional embodiment of the control system 600. In the system 600, as shown in FIG. 5A, adjustments to the metering point 30b are found by multiplying a new gear ratio (e.g., gear ratio trim) by master line or pitched unit operation velocity ($K_{PPS}$). The master line may be referred to as the independent axis and the controlled web 30 may be referred to as a dependent axis. In contrast, the system 600 as shown in FIG. 5B may derive adjustments to the actuator 30b by finding an actuator velocity trim and summing it with a feedforward actuator velocity, as shown below. This may be referred to as summing two jog commands (e.g., the actuator velocity trim and the feedforward actuator velocity).

In FIG. 5B, the controller 602 may operate as described above with respect to FIG. 5A up to the application of the nominal gear ratio 620. The gear ratio trim may then be scaled by a measure of master units per product, where product may represent one target object on a target web or one machine cycle of the pitched unit operation. The master units per product may be represented by $K_{mu}$. In addition, the master product velocity gain, $K_{PPS}$, may be applied within the controller 602 and prior to the zero order hold 622. It will be appreciated that, generally, the various gains downstream of the proportional 612 and integral terms 614 may be applied either inside or outside of the controller 602. The positions of the various scaling gains may affect the units of the output of the controller 602. For example, in the embodiment shown in FIG. 5B, the output of the controller 602 may be expressed as a controlled web velocity trim in rotary units of the controlled web per second.

At summing junction 704, the controlled web velocity trim may be summed with a feed forward controlled web actuator velocity. This value may be found by scaling the target product or pitched unit operation velocity ($K_{PPS}$) in products per second by $K_{mu}$. The result may be a target master velocity in master units per second. This value, in turn, may be scaled by the nominal gear ratio at 720 to generate the feed forward controlled web actuator velocity. The sum of the feed forward controlled web actuator velocity and the controlled web actuator velocity trim at junction 704 may provide a target controlled web actuator velocity. This value may be utilized to adjust the speed of the metering point 30b. The metering point 30b is modeled by the ideal actuator dynamics 706 summed with actuator or metering point disturbances at summing junction 708.

Inherent process gains 710 and 712 may result in an ideal controlled web pitch at the actual actuator velocity. Gain 710 may represent the inverse of the ratio of rotary units of the controlled web per meter. Gain 712 may represent the inverse of the target product pitch. Disturbances of the controlled web may be considered at summing junction 714, resulting in an actual controlled web velocity. This value is summed with an actual pitched unit operation velocity at summing junction 716 to find an actual pitched unit operation velocity relative to the actual controlled web velocity. The actual pitched unit operation velocity may be found, for example, starting with the target master velocity. This value may be scaled by an ideal pitched unit operation actuator dynamics and then converted to a velocity in products per second by scaling by $1/K_{mu}$ at 724. Disturbances in the pitched unit operation may be summed in at summing junction 726, resulting in the actual pitched unit operation velocity. It will be appreciated that the process variable 624 shown in FIG. 5A is also present in FIG. 5B, but is expressed as three discrete components 702, 710 and 712.

According to the embodiments shown in FIGS. 5A and 5B, values for the proportional term 612 ($K_{OP}$) and integral term 614 ($K_{OI}$) of the controller 602 may be found according to any suitable method. For example, given the registration process model 630, the equivalent continuous time open loop transfer function of the system 600 may be expressed as shown by Equation (7) below:

$$\frac{K_{OP}K_{PPS}e^{-T_Ds}(K_{OI}K_{PPS}+s)}{s^2} \quad (7)$$

The open loop Bode cross-over frequency may be expressed as shown by Equation (8) below:

$$K_{OP}K_{PPS} \text{ (rad/sec)} \quad (8)$$

Accordingly, $\tau$, a time constant of the controller 602 in seconds, may be expressed as the inverse of the cross-over frequency, or Equation (9) below:

$$\tau = \frac{1}{CrossOver} = \frac{1}{K_{OP}K_{PPS}} \text{(sec)} \quad (9)$$

A time constant, $\tau$, may be expressed in terms of a product time constant, $\tau_P$, of the controller 602 expressed in pre-produced objects, as shown by Equation (10) below:

$$\tau = \frac{\tau_P}{K_{PPS}} \text{(sec)} \quad (10)$$

Substituting Equation (10) into Equation (9) and solving for the proportional term 612 of the controller ($K_{OP}$) yields Equation 11 below:

$$K_{OP} = \frac{1}{\tau_P}(1/\text{products}) \quad (11)$$

The equivalent closed loop transfer function of the system 600 is given by Equation (12) below:

$$\frac{K_{OP}K_{PPS}e^{-T_Ds}(K_{OI}K_{PPS}+s)}{s^2+K_{OP}K_{PPS}e^{-T_Ds}s+K_{OP}K_{PPS}e^{-T_Ds}K_{OI}K_{PPS}} \quad (12)$$

The classic closed loop transfer function is given by Equation (13) below:

$$\frac{K\omega_n^2(\beta s+1)}{s^2+2\zeta\omega_n s+\omega_n^2} \quad (13)$$

where $\zeta$ is a unitless damping factor and $\omega_n$ is a natural frequency of the system 600 expressed in radians per second. Values for $\zeta$ and $\omega_n$ may be preset and/or received from a user of the system 600. Setting $T_D$ equal to zero and solving for $K_{OP}$, $K_{OI}$ may result in Equation (14) below:

$$K_{OI} = \frac{1}{4\tau_p\zeta^2}(1/\text{product} - \text{product\_periods}) \quad (14)$$

where $T_P$ is product or pitched unit operation period time unit.

In an alternative derivation, $K_{OP}$ and $K_{OI}$ may be expressed as shown below:

$$K_{OP} = \frac{4\tau_P + T_{DP}}{(2\tau_P + T_{DP})^2}(1/\text{products}) \quad (15)$$

$$K_{OI} = \frac{1}{4\tau_P\zeta^2 + T_{DP}}(1/\text{product} - \text{product\_periods}) \quad (16)$$

In Equations (15) and (16), $T_D$ may refer to system dead time and $T_{DP}$ is equal to $T_D * K_{pps}$.

According to various embodiments, the controller 602 may be constructed in independent form. For example, in the dependent form shown in FIGS. 5A and 5B, the input to the integral term 614 is scaled by the proportional term 612. In independent form, the input to the integral term 614 may be simply the error signal 606. Equations 17 and 18 illustrate example independent derivations of $K_{OP}$ and $K_{OI}$:

$$K_{OP\_I} = K_{OP} = \frac{1}{\tau_P}(1/\text{products}) \quad (17)$$

$$K_{OI\_I} = K_{OP} * K_{OI} = \frac{1}{4\tau_P^2\zeta^2}(1/\text{product} - \text{product periods}) \quad (18)$$

As demonstrated above with reference to Equations (6)-(18), the gains of the proportional 212 and integral 214 terms of the controller 602 may be expressed in terms of products or pre-produced objects and independent of time or line speed. Accordingly, the proportional 212 and integral 214 terms of the controller 602 may be set independent of any particular installation of the pitched unit operation. The velocity of the pitched unit operation and/or target web ($K_{PPS}$) may be taken by the system 600 as input, as shown above in FIGS. 5A and 5B. In this way, the closed-loop response of the system may be independent of line rate. The time response of the system may change. In terms of products, however, the response may be consistent. This may be superior to existing methods where the terms of PI controllers must be separately derived for each installation, often in the field.

It will be appreciated that the system 600 illustrated in FIGS. 5A and 5B may represent computer implemented control components, effects due to metering points, pitched unit operations, as well as effects of other mechanical properties of the production line. For example, the controller 602 may be implemented by any suitable type of computer hardware including, for example, any kind of processor or processors with associated memory for storing instructions, an application specific integrated circuit (ASIC), a field programmable gate array (FPGA), etc.

Disposable diaper products typically include a topsheet material, an absorbent core, and a backsheet material. The topsheet material is located to be placed facing the body or nearest the body when the diaper is worn and is generally provided with a liquid permeable region so that body exudates can flow through the topsheet to the absorbent core, where they are contained. The backsheet material, which is placed away from the body during wear, is typically liquid impermeable so that outer clothing or other articles such as bedsheets are not wetted by the body exudates. Such an exemplary diaper is disclosed in, for example, Buell U.S. Pat. No. 5,569,234, directed to a "Disposable Pull-on Pant".

In addition to the basic topsheet, core, and backsheet components, it will be understood by those of skill in the art that many other features for disposable absorbent articles are within the scope of the present invention. For example, barrier cuffs as described in Lawson and Dragoo U.S. Pat. Nos. 4,695,278 and 4,795,454 are a desirable feature for disposable absorbent articles. In addition, skin care type topsheets that are provided with lotion thereon for the purpose of reducing skin irritation and chafing are a desirable feature herein.

Figure 6:
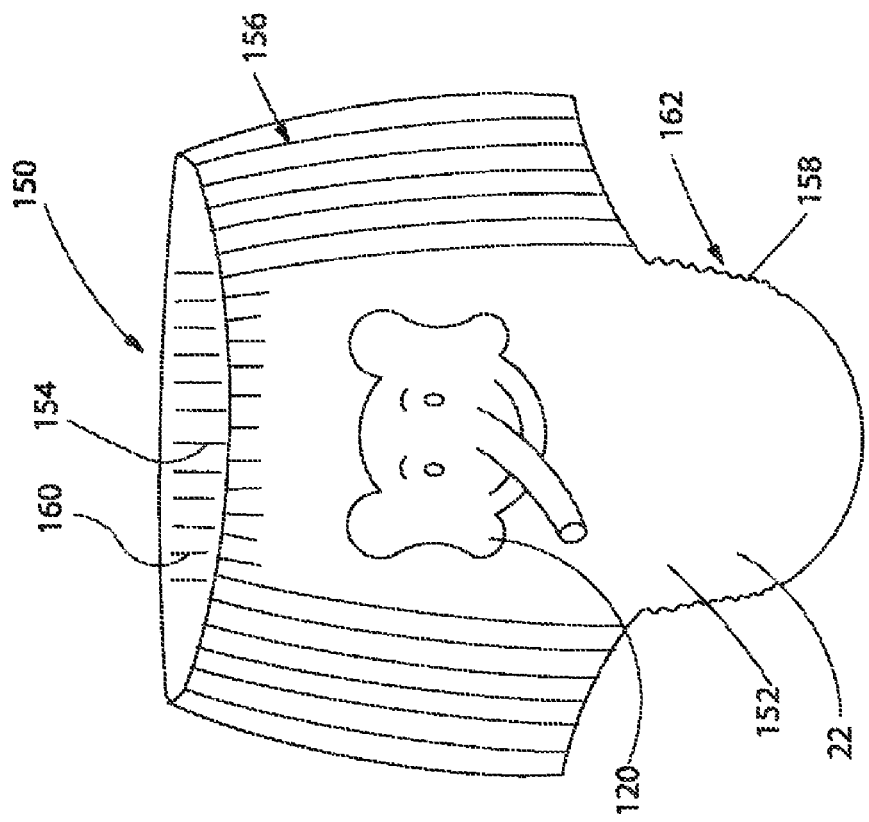
FIG. 6 is a front view of a one embodiment of a disposable absorbent article having registered graphics.

Referring to FIG. 6, there is shown an exemplary disposable pull-on diaper 150, which is generally pulled onto the body of the wearer by inserting the legs into the leg openings 162 and pulling the article up over the waist. Generally, "pull-on diaper" refers to pull-on garments worn by small children and other incontinent individuals to absorb and contain body exudates. It should be understood that other pull-on garments such as training pants, incontinent briefs, feminine briefs, feminine hygiene garments or panties, and like, are included herein.

Referring to FIGS. 6 and 7, the diaper 150 is generally comprised of a backsheet 152, a topsheet 154 and an absorbent layer 156 (shown in dashed lines in FIG. 8) located between the backsheet 152 and the topsheet 154. The backsheet 154 is the surface which faces away from the wearer's body, while the topsheet 152 is the surface which faces toward the wearer's body. In one embodiment of the present invention, the backsheet 152 is comprised of at least a microporous polymer film printed with pre-produced objects 22 (e.g., graphics 120, 122) as described herein. The backsheet 152 may further comprise a layer of nonwoven material laminated or otherwise secured to the microporous film layer, in which case there is provided a more cloth-like and garment-like feel. In such a case, the nonwoven web may be fed to the web handling process as a continuous incoming web and may be combined in a desired relationship with the controlled web 30 and the target web 40.

In the case of a laminated nonwoven backsheet, it is desirable that the surface texture of the non-woven not be impacted by a laminated sublayer, (e.g., a microporous polymer film sublayer), which pulls it back and causes it to "pucker." It is more desirable that any puckering that is required for the operation of a registration system be limited to the underlying polymer material, which is neither seen nor felt by the user of the product. The system of the present invention can be used in cases where the pitch length Lpp of the microporous film web (controlled web 30) may be longer or shorter than that of the product, Ltp. Overfeeding the target web may lead to superior surface texture. After the final cut, when Lpp is less than Ltp, the film material pulls back the nonwoven material that forms part of the product. This creates a roughened texture of the exposed surface of the laminates where the consumer can see and feel. This, when Lpp is greater than Ltp, the impact of the unequal combining upon which the registration systems depends is hidden from the consumer. In general, Lc should be greater than both Lpp and Ltp, to avoid the possibility of a zero-tension situation.

Elastically extensible side panels 156 are provided to ensure more comfortable and contouring fit by initially conformably fitting the pull-on diaper 150 to the wearer and sustaining this fit throughout the time of wear well past when it has been loaded with exudates. Leg elastics 158 and waist elastic region 160 are also provided to enhance the fit around the legs and waist, respectively.

FIG. 6 shows the front view of the diaper 150 with an exemplary pre-produced object graphic 120 positioned in about the upper region of the backsheet, on the back side of the diaper 150. In FIG. 8, there is shown a simplified plan view of an embodiment of a disposable absorbent article in its flat, uncontracted state prior to formation pre-produced object 22, graphic 120 is shown in the back region of the diaper with graphic 122 additionally shown in the front region of the diaper.

It is understood that the examples and embodiments described herein are for illustrative purposes only and that various modifications or changes in light thereof will be suggested to one of skill in the art without departing from the scope of the present invention.

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to that extent that any meaning or definition of a term in this document conflicts with any meaning or definition of the same term is a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A computer-implemented method for registering a controlled web to an on-line pitched unit operation with a machine cycle, the controlled web comprising a plurality of pre-produced objects longitudinally spaced apart at a pitch interval, the method comprising:
   receiving one or more signals that represent a presence of each of the pre-produced objects;
   generating actual position bias data based, at least in part, on the signals, wherein the actual position bias data represent, for each of the pre-produced objects, an actual position of the pre-produced object relative to a machine cycle position of the pitched unit operation;
   generating a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generating an integral term, at least in part by summing the plurality of error signals;

generating a correction signal, at least in part by summing the integral term and a proportional term;

generating a gear ratio trim value by scaling the correction signal by a nominal gear ratio, wherein the nominal gear ratio is proportional to a translation of the controlled web over a corresponding translation of the pitched unit operation; and registering the controlled web to the pitched unit operation based, at least in part, on the gear ratio trim value;

wherein the generating of the integral term includes generating the integral term that is proportional to the inverse of a target time constant expressed in pre-produced objects.

2. A computer-implemented method for registering a controlled web to an on-line pitched unit operation with a machine cycle, the controlled web comprising a plurality of pre-produced objects longitudinally spaced apart at a pitch interval, the method comprising:

receiving one or more signals that represent a presence of each of the pre-produced objects;

generating actual position bias data based, at least in part, on the signals, wherein the actual position bias data represent, for each of the pre-produced objects, an actual position of the pre-produced object relative to a machine cycle position of the pitched unit operation;

generating a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generating an integral term, at least in part by summing the plurality of error signals;

generating a correction signal, at least in part by summing the integral term and a proportional term;

generating a gear ratio trim value by scaling the correction signal by a nominal gear ratio, wherein the nominal gear ratio is proportional to a translation of the controlled web over a corresponding translation of the pitched unit operation; and registering the controlled web to the pitched unit operation based, at least in part, on the gear ratio trim value;

wherein the generating of the integral term includes generating the integral term that is proportional to:

$$\frac{1}{4\tau_P \zeta^2}$$

wherein $\tau_P$ is a target time constant expressed in pre-produced objects; and wherein $\zeta$ is a damping factor.

3. A computer-implemented method for registering a controlled web to an on-line pitched unit operation with a machine cycle, the controlled web comprising a plurality of pre-produced objects longitudinally spaced apart at a pitch interval, the method comprising:

receiving one or more signals that represent a presence of each of the pre-produced objects;

generating actual position bias data based, at least in part, on the signals, wherein the actual position bias data represent, for each of the pro-produced objects, an actual position of the pre-produced object relative to a machine cycle position of the pitched unit operation;

generating a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generating an integral term, at least in part by summing the plurality of error signals;

generating a correction signal, at least in part by summing the integral term and a proportional term;

generating a gear ratio trim value by scaling the correction signal by a nominal gear ratio, wherein the nominal gear ratio is proportional to a translation of the controlled web over a corresponding translation of the pitched unit operation;

registering the controlled web to the pitched unit operation based, at least in part, on the gear ratio trim value; and generating the proportional term that is proportional to:

$$\frac{1}{\tau_P}$$

wherein $\tau_P$ is a target time constant expressed in pre-produced objects.

4. A computer-implemented method for registering a controlled web to an on-line pitched unit operation with a machine cycle, the controlled web comprising a plurality of pre-produced objects longitudinally spaced apart at a pitch interval, the method comprising:

receiving one or more signals that represent a presence of each of the pre-produced objects;

generating actual position bias data based, at least in part, on the signals, wherein the actual position bias data represent, for each of the pre-produced objects, an actual position of the pre-produced object relative to a machine cycle position of the pitched unit operation;

generating a plurality or error signals that represent, for each of the pre-produced objects, a difference between a target position bias constant and the actual position bias data, wherein the target position bias constant represents a desired position of the pre-produced object relative to the machine cycle position of the pitched unit operation;

generating an integral term, at least in part by summing the plurality of error signals;

generating a correction signal, at least in part by summing the integral term and a proportional term;

generating a gear ratio trim value by scaling the correction signal by a nominal gear ratio, wherein the nominal gear ratio is proportional to a translation of the controlled web over a corresponding translation of the pitched unit operation;

registering the controlled web to the pitched unit operation based, at least in part, on the gear ratio trim value;

scaling the gear ratio trim to generate a controlled web velocity trim; and generating a target actuator velocity by summing the controlled web velocity trim with a feed forward controlled web velocity;

wherein the registering includes registering the controlled web to the pitched unit operation based, at least in part, on the target actuator velocity.

5. A computer-implemented method for registering a controlled web to an on-line pitched unit operation with a machine cycle, the controlled web comprising a plurality of pre-produced objects longitudinally spaced apart at a pitch interval, the method comprising:

receiving one or more signals that represent a presence of each of the pre-produced objects;

generating actual position bias data based, at least in part, on the signals, wherein the actual position bias data represent, for each of the pre-produced objects, an actual position of the pre-produced object relative to a machine cycle position of the pitched unit operation;

generating a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generating an integral term, at least in part by summing the plurality of error signals;

generating a correction signal, at least in part by summing the integral term and a proportional term;

generating a gear ratio trim value by scaling the correction signal by a nominal gear ratio, wherein the nominal gear ratio is proportional to a translation of the controlled web over a corresponding translation of the pitched unit operation;

registering the controlled web to the pitched unit operation based, at least in part, on the gear ratio trim value;

wherein the receiving includes receiving one or more signals that represent a presence of each of the pre-produced objects at a predetermined location;

for each of the pre-produced objects, sensing a machine cycle position of the pitched unit operation;

for each of the pre-produced objects, calculating a difference between the predetermined location and the machine cycle position of the pitched unit operation; and wherein the generating of the actual position bias data comprises generating actual position bias data based, at least in part, on the difference, for each of the pre-produced objects.

6. The method of claim 5, wherein the sensing of the machine cycle position includes reading a position sensing device of the pitched unit operation.

7. The method of claim 5, wherein the sensing of the machine cycle position includes capturing an image of product after the pitched unit operation.

8. A computer-implemented system for registering a controlled web to an on-line pitched unit operation with a machine cycle, the controlled web comprising a plurality of pre-produced objects longitudinally spaced apart at a pitch interval, the system comprising a computer device comprising at least one processor and operatively associated memory, wherein the memory comprises instruction that, when executed by the at least one processor, causes the computer device to:

receive one or more signals that represent a presence of each of the pre-produced objects;

generate actual position bias data based, at least in part, on the signals, wherein the actual position bias data represent, for each of the pre-produced objects, an actual position of the pre-produced object relative to a machine cycle position of the pitched unit operation;

generate a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generate an integral term, at least in part by summing the plurality of error signals;

generate a correction signal, at least in part by summing the integral term and a proportional term;

generate a gear ratio trim value by scaling the correction signal by a nominal gear ratio, wherein the nominal gear ratio is proportional to a translation of the controlled web over a corresponding translation of the pitched unit operation; and register the controlled web to the pitched unit operation based, at least in part, on the gear ratio trim value;

wherein the memory further comprises instructions that, when executed by the at least one processor, causes the computer device to generate the integral term that is proportional to the inverse of a target time constant expressed in pre-produced objects.

9. A computer-implemented system for registering a controlled web to an on-line pitched unit operation with a machine cycle, the controlled web comprising a plurality of pre-produced objects longitudinally spaced apart at a pitch interval, the system comprising a computer device comprising at least one processor and operatively associated memory, wherein the memory comprises instructions that, when executed by the at least one processor, causes the computer device to:

receive one or more signals that represent a presence of each of the pre-produced objects;

generate actual position bias data based, at least in part, on the signals, wherein the actual position bias data represent, for each of the pre-produced objects, an actual position of the pre-produced object relative to a machine cycle position of the pitched unit operation;

generate a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generate an integral term, at least in part by summing the plurality of error signals;

generate a correction signal, at least in part by summing the integral term and a proportional term;

generate a gear ratio trim value by scaling the correction signal by a nominal gear ratio, wherein the nominal gear ratio is proportional to a translation of the controlled web over a corresponding translation of the pitched unit operation; and register the controlled web to the pitched unit operation based, at least in part, on the gear ratio trim value;

wherein the memory further comprises instructions that, when executed by the at least one processor, causes the computer device to generate the integral term that is proportional to:

$$\frac{1}{4\tau_P \zeta^2}$$

wherein $\tau_P$ is a target time constant expressed in pre-produced objects; and where $\zeta$ is a damping factor.

10. A computer-implemented system for registering a controlled web to an on-line pitched unit operation with a machine cycle, the controlled web comprising a plurality of pre-produced objects longitudinally spaced apart at a pitch interval, the system comprising a computer device comprising at least one processor and operatively associated memory, wherein the memory comprises instructions that, when executed by the at least one processor, causes the computer device to:

receive one or more signals that represent a presence of each of the pre-produced objects;

generate actual position bias data based, at least in part, on the signals, wherein the actual position bias data represent, for each of the pre-produced objects, an actual position of the pre-produced object relative to a machine cycle position of the pitched unit operation;

generate a plurality of error signals that represent, for each of the pre-produced objects, a difference between a target position bias constant and the actual position bias data, wherein the target position bias constant represents a desired position of the pre-produced object relative to the machine cycle position of the pitched unit operation;

generate an integral term, at least in part by summing the plurality of error signals;

generate a correction signal, at least in part by summing the integral term and a proportional term;

generate a gear ratio trim value by scaling the correction signal by a nominal gear ratio, wherein the nominal gear ratio is proportional to a translation of the controlled web over a corresponding translation of the pitched unit operation; and register the controlled web to the pitched unit operation based, at least in part, on the gear ratio trim value;

wherein the memory further comprises instructions that, when executed by the at least one processor, causes the computer device to generate the proportional term that is proportional to:

$$\frac{1}{\tau_P}$$

wherein $\tau_P$ is a target time constant expressed n pre-produced objects.

* * * * *

UNITED STATES PATENT AND TRADEMARK OFFICE
CERTIFICATE OF CORRECTION

PATENT NO. : 8,244,393 B2
APPLICATION NO. : 12/556922
DATED : August 14, 2012
INVENTOR(S) : Jon Kevin McLaughlin et al.

It is certified that error appears in the above-identified patent and that said Letters Patent is hereby corrected as shown below:

Claim 3

Line 3, delete "pro-produced" and insert -- pre-produced --.

Signed and Sealed this
Twenty-second Day of January, 2013

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,244,393 B2 | Page 1 of 1 |
| APPLICATION NO. | : 12/556922 | |
| DATED | : August 14, 2012 | |
| INVENTOR(S) | : Jon Kevin McLaughlin et al. | |

It is certified that error appears in the above-identified patent and that said Letters Patent is hereby corrected as shown below:

Column 18, line 3 (Claim 3, line 10), delete "pro-produced" and insert -- pre-produced --.

This certificate supersedes the Certificate of Correction issued January 22, 2013.

Signed and Sealed this
Nineteenth Day of February, 2013

Teresa Stanek Rea
*Acting Director of the United States Patent and Trademark Office*